United States Patent [19]

Ebinger et al.

[11] Patent Number: 4,789,401

[45] Date of Patent: Dec. 6, 1988

[54] SOLUBLE COLLAGEN SPONGE

[75] Inventors: Jürgen Ebinger, Eppstein; Rolf-Dieter Beutler, Frankfurt am Main; Helmut Lindner, Grasellenbach, all of Fed. Rep. of Germany

[73] Assignee: Merz+Co. GmbH & Co., Frankfurt am Main, Fed. Rep. of Germany

[21] Appl. No.: 876,824

[22] Filed: Jun. 20, 1986

[30] Foreign Application Priority Data

Jun. 25, 1985 [DE] Fed. Rep. of Germany ....... 3522626

[51] Int. Cl.$^4$ .................... C08L 89/06; A61F 13/16
[52] U.S. Cl. ................................. 106/122; 106/155; 106/161; 604/368; 604/369; 514/947; 514/950
[58] Field of Search ................. 106/122, 155, 161; 604/368, 369; 514/947, 950

[56] References Cited

U.S. PATENT DOCUMENTS

| | | | |
|---|---|---|---|
| 3,157,524 | 11/1964 | Artandi | 106/122 |
| 4,279,812 | 7/1981 | Cioca | 604/368 |
| 4,295,894 | 10/1981 | Cioca et al. | 106/155 |
| 4,412,947 | 11/1983 | Cioca | 106/155 |

OTHER PUBLICATIONS

Das Leder, 12th edition, No. 9, Sep. 1961, pp. 213-222+translation of pp. 213 and 214.
Das Leder, 29th vol., No. 3, Mar. 1978, pp. 33-41 plus translation of pp. 36 and 40.
Kollagen by Verlag Theodore Steinkopf, Dresden 1966, pp. 82, 119, 120 & 121, cover sheet and translation of relevant portions.

*Primary Examiner*—Theodore Morris
*Attorney, Agent, or Firm*—Gordon W. Hueschen

[57] ABSTRACT

The invention concerns a collagen sponge which has a denaturation temperature of at least 37° C., is not cross-linked and in one of its two embodiments forms an optically clear solution in aqueous medium. As compared with the collagen sponges previously known, it is particularly suitable as support material for pharmaceutical and cosmetic active substances since it has a higher denaturation temperature than the latter and dissolves again in contact with body fluid. The collagen sponge of the invention is prepared from an optically clear collagen solution by precipitation with neutral salts, dissolving and reprecipitation and then subjecting the collagen to freeze-drying without removal of the precipitation salt. Acid-swollen collagens and/or cellulose or cellulose derivatives can also be added to the solution, whereby the physical properties of the collagen sponge can be affected.

9 Claims, No Drawings

SOLUBLE COLLAGEN SPONGE

The object of the invention is a collagen sponge which dissolves in aqueous solution or in contact with body fluids and has a denaturing temperature of at least 37° C. Such a collagen sponge is particularly suitable as support for pharmaceutically and cosmetically active substances.

Support materials of collagen of sponge-like or felt-like structure are already known. However, they have too low a denaturation temperature and, in particular, do not dissolve in aqueous medium or in body fluids. These collagen support materials of the prior art are produced as a rule by cross-linking reactions, for instance with aldehydes.

There is the drawback in the use of such cross-linked collagen products as supports for active substances that they can cause inflammations, defense reactions or the formation of foreign-body giant cells in the body. The collagen product obtained by the cross-linking is insoluble with respect to physiological solutions as well as body fluids, so that manual removal from body cavities (for instance the vaginal cavity) is necessary after application.

These previously-described collagen products furthermore have the disadvantage that irreversible cross-linkings are produced by the drying of the collagen and thus a loss or a considerable reduction of solubility occurs even if soluble collagen is used as initial solution. The collagen products known up to the present time do not have the ability to again form an optically-clear collagen solution by addition of water or body fluids and they must thus be removed manually after application, which represents a substantial disadvantage, for instance, in the case of intravaginal use (toxic shock syndrome). These disadvantages are avoided by the collagen sponge of the invention.

The collagen sponge of the invention is produced by the method described below. One preferably starts from skins of young mammals, the skins being first of all cleaned in customary manner. After the cleaning, the soluble collagen is extracted from the insoluble parts of the skins by acids, preferably organic acids of low molecular weight, a molecular weight of not more than 200 being particularly preferred. In the preparation of this initial solution, it should be seen to it, by controlling the extraction or concentration of the collagen and by means of polarimetric measurements, that a true, i.e. optically clear, solution is obtained. The collagen contained in this solution has a denaturation temperature of at least 37° C., and preferably 39° to 45° C.

The collagen is precipitated from the solution—possibly with several repetitions—by neutral salts, preferably sodium chloride or sodium sulfate. The salt concentration—referred to the volume of the total solution —is preferably 3 to 5% by weight. It is important, in accordance with the invention, that the precipitation salt or a part thereof remain in the precipitated collagen and is therefore not removed from it by dialysis or other methods. In this way, a salt-containing intermediate phase of solid or almost solid consistency is obtained which has a collagen content of about 20 to 40 wt %.

This intermediate phase is dissolved again to a collagen content of less than 20 to 40 wt %, and preferably 0.1 to 3 wt %. The solution thus obtained is subjected to freeze-drying in several steps. First of all, a shock freezing is effected, the development of ice crystals which can be noted by the naked eye being prevented by customary means such as shaking or stirring the solution. Thereupon it is further cooled to about −25° C. to −40° C. and set aside for a few hours until fibers or fibrils are formed in the collagen phase. This is finally followed by the actual freeze-drying, i.e. with the application of vacuum.

In this way, a collagen sponge is obtained which is denatured only at at least 37° C., and preferably 39° to 45° C., which is not cross-linked and which forms, in aqueous medium, an optically clear solution which therefore does not cause any refraction in polarized light. The density of this collagen sponge is preferably 15 to 35 mg/cm$^3$. Depending on the shape of the vessel in which the freeze-drying is effected, different shapes (for instance cylindrical segments, spherical segments) can be obtained and the collagen product, due to its sponge-like structure, can easily be brought into any desired size or shape such as is necessary for the specific purpose or use.

Furthermore, the physical properties of the sponge (strength, resilience) can be controlled via the initial content of soluble collagen prior to the freeze-drying, so that particularly advantageous embodiments for specific applications can be created also by such control of the physical properties.

The physical properties can also be controlled by adding acid-swollen collagens, which as such do not form an optically clear solution, and/or cellulose or cellulose derivatives to the collagen which forms an optically clear solution. This is advisedly done after the precipitation by neutral salts in the solution which is thereupon again formed. The addition can also be effected, however, already in the initial solution prior to the precipitation. The solubility and the rate of solution of the collagen sponge finally obtained decreases with the quantity of the aforementioned added substances and it is imparted greater stability against external influences such as moisture, compression and tension. Such a product is, in particular, desirable if it is to be used not in the vaginal region but topically and therefore when a longer life of the collagen sponge is desired, as for instance for the purpose of the occlusion of open wounds.

However, it has been found that the proportion of the acid-swollen collagen and/or the cellulose or cellulose derivatives should not be greater than 65% in proportion to the collagen forming an optically clear solution since above this percentage there may finally be obtained a collagen sponge which is insoluble. The denaturation temperature and the density of the collagen sponge are not substantially changed by the additions in question here.

The incorporation of the pharmaceutically or cosmetically active substances into the final collagen sponge can be effected in customary manner. The active substance, however, is preferably introduced into one of the collagen solutions described above and, with particular preference, into that solution which is diluted to a collagen content of less than 20 to 40 wt % and which is then subjected to the freezing steps. This preferred method makes it possible to use smaller amounts of active substance and furthermore leads to a particularly uniform distribution of the active substance in the collagen sponge.

The advantage of the collagen sponge of the invention consists, in general, in the fact that by the development of fibrils or fibers there is developed a fine-pore, uniform, sponge-like collagen structure which, upon contact with water or body fluids, again forms, upon dissolving, an optically-clear collagen solution. It is thus no longer necessary manually to remove the collagen sponge after the application.

Additional advantages are:

Since, aside from the support material of the invention, no further auxiliary substances need be incorporated into the preparation, intolerance phenomena are reduced to a minimum.

For use in body cavities, application can be effected without prior impregnation with water, as a result of which a loss of active substance by water contact is avoided and the danger of contamination is reduced.

The active substances are completely liberated since the support material dissolves completely.

The soluble collagen sponge makes possible a substantially smaller amount of active substances, for instance contraceptives, as compared with insoluble support material.

Finally, there are also no problems with respect to disposal.

The possibilities of use of the collagen sponges provided with active substances in accordance with the invention are manifold. Thus collagen sponges of the invention which are provided, for instance, with disinfectants, antiseptics, wound-treatment agents, antibiotics, or chemotherapeutic agents can be applied to the skin, the mucous membrane, or wounds. Collagen sponges according to the invention which are provided with the corresponding active substances are very particularly suitable for introduction into body cavities, such as the anus, vagina, nose, or ear. The collagen sponge of the invention is particularly preferred as support material for contraceptives for introduction into the vagina.

We claim:

1. A collagen sponge, characterized by the fact that it has a denaturation temperature of at least 37° C., is not cross-linked and has a density of 15 to 35 mg/cm$^3$.

2. A collagen sponge according to claim 1, characterized by the fact that it forms an optically-clear solution in aqueous medium.

3. A collagen sponge according to claim 1 or 2, characterized by the fact that it contains a pharmaceutically or cosmetically active substance incorporated therein.

4. A method of producing collagen sponge according to claim 1 or 2 or 3 starting from an acid, optically-clear soluble collagen solution obtained from skins of young mammals, comprising the following method steps:
   (a) precipitating the collagen from the solution by addition of neutral salt;
   (b) recovering and redissolving the precipitated collagen to a lower collagen content;
   (c) shock-freezing the resulting salt-containing intermediate phase soluble collagen solution while preventing the development of ice crystals which can be noted by the naked eye;
   (d) further cooling the solution until fibers or fibrils are formed in the collagen phase; and
   (e) freeze-drying the solution with the application of vacuum to give the desired product.

5. The method of claim 4 of preparing a collagen sponge containing a pharmaceutically- or cosmetically-active substance, characterized by the fact that the active substance
   (a) is brought into contact with the preformed solid collagen sponge isolated from the solution, or
   (b) is introduced into the soluble collagen solution at step (b) thereof.

6. The method of claim 4 wherein the neutral salt is sodium chloride or sodium sulfate.

7. The method of claim 4 comprising adding an acid-swollen collagen and/or cellulose or cellulose derivative to the solution.

8. The method of claim 4, wherein the precipitation in step (a) is effected by the addition of about 3 to 5% by weight of a neutral salt selected from sodium chloride and sodium sulfate, wherein the precipitated collagen recovered in step (b) has a 20 to 40 weight percent collagen content, wherein the recovered precipitated collagen in step (b), having a 20–40 weight percent collagen content, is redissolved to a lower collagen content of between about 0.1 to 3 weight percent, and wherein the solution is cooled in step (d) to about −25 to −40° C. to effect formation of fibers or fibrils in the collagen phase.

9. A collagen sponge according to claim 1 or 2 or 3, containing in addition acid-swollen collagen and/or cellulose or cellulose derivative in an amount which does not substantially change the denuaturation temperature or density of the collagen sponge.

* * * * *